US007477156B2

(12) United States Patent
Long et al.

(10) Patent No.: US 7,477,156 B2
(45) Date of Patent: Jan. 13, 2009

(54) CONNECTION MECHANISMS IN ABSORBENT ARTICLES FOR BODY FLUID SIGNALING DEVICES

(75) Inventors: Andrew Mark Long, Appleton, WI (US); Christopher Peter Olson, Neenah, WI (US); Shirlee A. Weber, Neenah, WI (US); Tom M. Ales, Neenah, WI (US); Robert Samuel Schlaupitz, New London, WI (US); Robert D. Wright, Peachtree City, GA (US); George I. Nukuto, Neenah, WI (US); Shawn J. Sullivan, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 223 days.

(21) Appl. No.: 11/405,263

(22) Filed: Apr. 17, 2006

(65) Prior Publication Data

US 2007/0024457 A1    Feb. 1, 2007

Related U.S. Application Data

(63) Continuation-in-part of application No. 11/119,377, filed on Apr. 29, 2005, now Pat. No. 7,394,391.

(51) Int. Cl.
*G08B 23/00* (2006.01)
*G08B 21/00* (2006.01)
*A61M 1/00* (2006.01)

(52) U.S. Cl. .................... 340/573.5; 340/604; 604/318

(58) Field of Classification Search ............ 340/573.5, 340/604, 605; 604/318; 318/643; 73/335.06, 73/335.02

See application file for complete search history.

(56) References Cited

U.S. PATENT DOCUMENTS 3,759,246 A    9/1973 Flack et al.

(Continued)

FOREIGN PATENT DOCUMENTS

EP    1047033 A1    10/2000

(Continued)

OTHER PUBLICATIONS

Product Information on Surface Electrodes—Disc (Disc Electrodes) from Bio-logic Systems Corp., 8 pages.

(Continued)

*Primary Examiner*—George A Bugg
*Assistant Examiner*—Jennifer Mehmood
(74) *Attorney, Agent, or Firm*—Dority & Manning, P.A.

(57) ABSTRACT

Absorbent articles incorporating a wetness sensor for indicating the presence of a body fluid are disclosed. In particular, the absorbent articles include at least two conductive elements that form an open circuit within the article. Each conductive element is connected to a conductive pad member that has sufficient surface area in order to facilitate connection to a signaling device. In accordance with the present disclosure, various attachment mechanisms are disclosed for attaching the pad members to a signaling device. In particular, although the absorbent articles are disposable, the signaling device is intended to be used with multiple absorbent articles. Therefore, a simple and efficient method of connecting the signaling device to the pad members provides various advantages. In one particular embodiment, for instance, the pad members comprise a conductive loop-type material that is attached to a corresponding conductive hook-type material on the signaling device.

24 Claims, 12 Drawing Sheets

U.S. PATENT DOCUMENTS

| | | | |
|---|---|---|---|
| 3,864,676 A | 2/1975 | Macias et al. |
| 4,100,324 A | 7/1978 | Anderson et al. |
| 4,106,001 A | 8/1978 | Mahoney |
| 4,191,950 A | 3/1980 | Levin et al. |
| 4,205,672 A | 6/1980 | Dvorak |
| 4,356,818 A | 11/1982 | Macias et al. |
| 4,539,559 A | 9/1985 | Kelly et al. |
| 4,653,491 A | 3/1987 | Okada et al. |
| 4,704,108 A | 11/1987 | Okada et al. |
| 4,704,116 A | 11/1987 | Enloe |
| 4,768,023 A | 8/1988 | Xie |
| 4,940,464 A | 7/1990 | Van Gompel et al. |
| 5,284,703 A | 2/1994 | Everhart et al. |
| 5,350,624 A | 9/1994 | Georger et al. |
| 5,486,166 A | 1/1996 | Bishop et al. |
| 5,490,846 A | 2/1996 | Ellis et al. |
| 5,557,263 A | 9/1996 | Fisher et al. |
| 5,760,694 A | 6/1998 | Nissim et al. |
| 5,766,389 A | 6/1998 | Brandon et al. |
| 5,790,036 A | 8/1998 | Fisher et al. |
| 5,808,554 A | 9/1998 | Shuminov |
| 5,820,973 A | 10/1998 | Dodge, II et al. |
| 5,838,240 A | 11/1998 | Johnson |
| 5,845,644 A | 12/1998 | Hughes et al. |
| 6,075,178 A | 6/2000 | La Wilhelm et al. |
| 6,097,297 A | 8/2000 | Fard |
| 6,163,262 A | 12/2000 | Wu |
| 6,200,250 B1 | 3/2001 | Janszen |
| 6,246,330 B1 | 6/2001 | Nielsen |
| 6,399,853 B1 | 6/2002 | Roe et al. |
| 6,501,002 B1 | 12/2002 | Roe et al. |
| 6,559,772 B2 | 5/2003 | Zand et al. |
| 6,573,837 B2 | 6/2003 | Bluteau |
| 6,580,013 B1 | 6/2003 | Belloso |
| 6,583,722 B2 | 6/2003 | Jeutter et al. |
| 6,603,403 B2 | 8/2003 | Jeutter et al. |
| 6,645,190 B1 | 11/2003 | Olson et al. |

FOREIGN PATENT DOCUMENTS

| | | |
|---|---|---|
| EP | 1398014 A2 | 3/2004 |
| FR | 2788430 A3 | 7/2000 |
| GB | 2250121 A | 5/1992 |
| WO | WO 8401626 A1 | 4/1984 |
| WO | WO 9742613 A2 | 11/1997 |
| WO | WO 9742613 A3 | 11/1997 |
| WO | WO 9812997 A1 | 4/1998 |
| WO | WO 9951179 A1 | 10/1999 |
| WO | WO 0037009 A2 | 6/2000 |
| WO | WO 0037009 A3 | 6/2000 |
| WO | WO 02101679 A1 | 12/2002 |

OTHER PUBLICATIONS

Product Information on Anti Static Wrist Straps from NC Stat Corporation, Apr. 29, 2005, 5 pages, www.nccorporation.com.
Product Information on Conductive Hook and Loop Tape from Fastech of Jacksonville, Inc., Apr. 29, 2005, 2 pages, www.hookandloop.com.
PCT Search Report and Written Opinion for PCT/US2006/015862.

CONNECTION MECHANISMS IN ABSORBENT ARTICLES FOR BODY FLUID SIGNALING DEVICES

RELATED APPLICATIONS

The present application is a continuation-in-part application of U.S. patent application Ser. No. 11/119,377 (U.S. Pat. No. 7,394,391) filed on Apr. 29, 2005.

BACKGROUND OF THE INVENTION

Absorbent articles such as diapers, training pants, incontinence products, feminine hygiene products, swim undergarments, and the like conventionally include a liquid permeable body-side liner, a liquid impermeable outer cover, and an absorbent core. The absorbent core is typically located in between the outer cover and the liner for taking in and retaining liquids (e.g., urine) exuded by the wearer.

The absorbent core can be made of, for instance, superabsorbent particles. Many absorbent particles, especially those sold under the tradename HUGGIES™ by the Kimberly-Clark Corporation, are so efficient at absorbing liquids that it is sometimes difficult to tell whether or not the absorbent article has been insulted with a body fluid.

Accordingly, various types of moisture or wetness indicators have been suggested for use in absorbent articles. The wetness indicators may include alarm devices that are designed to assist parents or attendants identify a wet diaper condition early on. The devices produce either a visual or an audible signal.

In some embodiments, for instance, inexpensive conductive threads or foils have been placed in the absorbent articles in the machine direction. The conductive materials serve as conductive leads for a signaling device and form an open circuit in the article that can be closed when a body fluid, such as urine, closes the circuit. In these embodiments, although the absorbent articles may be disposable, the signaling devices are not. Thus, the signaling devices are intended to be removed from the article and reattached to a subsequent article.

Problems, however, have been encountered in designing an attachment mechanism for the signaling device that does not appreciably increase the cost of the absorbent article but allows for a very reliable attachment of the signaling device to the conductive leads. Further, problems have been experienced in designing an attachment mechanism that can be incorporated into the absorbent article during high speed manufacturing processes.

SUMMARY OF THE INVENTION

In general, the present disclosure is directed to improved attachment mechanisms for attaching signaling devices to disposable absorbent articles. The signaling device, for instance, may be configured to indicate to a user that a body fluid is present in the absorbent article. For example, in one embodiment, the absorbent article comprises a diaper and the signaling device is configured to indicate the presence of urine or of a bowel movement. In other embodiments, however, the signaling device may be configured to indicate the presence of yeast or metabolites depending upon the particular type of absorbent article that is used in conjunction with the signaling device.

In one embodiment, the absorbent article of the present invention includes conductive leads that extend, for instance, in the longitudinal direction of the article. The conductive leads can be made from relatively inexpensive materials and therefore can be disposable with the absorbent article. The signaling device, however, may be configured to be reused multiple times. Thus, the present disclosure is directed to a simple and efficient manner of attaching the signaling device to the absorbent article so that there is an electrical connection between the conductive leads and the signaling device.

In one particular embodiment, the absorbent article comprises a chassis including an outer cover having an interior surface and an exterior surface. An absorbent structure is positioned adjacent to the interior surface of the outer cover. If desired, a liquid permeable body-side liner may also be incorporated into the chassis on the opposite side of the absorbent structure. The chassis may include a crotch region positioned in between a front region and a back region. The front region and the back region may define a waist region therebetween.

First and second conductive elements may be contained in the chassis. The conductive elements may be made from, for instance, a conductive thread or a conductive foil, and may extend from the waist region to at least the crotch region of the chassis without intersecting. These conductive elements can form a simple open circuit (for wetness sensing for example) or can be connected to a sensor(s) for sensing temperature, chemical constituents, microbes or other physical or environmental conditions.

A first conductive pad member may be electrically connected to the first conductive element and a second conductive pad member may be electrically connected to the second conductive element. The conductive pad members, in one embodiment, may be positioned below at least one layer of material that forms part of the outer cover. By being positioned below at least one material layer, the conductive pad members are protected. Further, placing the pad members below at least one layer of material in the outer cover also facilitates commercial production of the absorbent article.

In general, the size of the conductive pad members may vary depending upon the particular application. The pad members, for example, may have any size sufficient to facilitate an electrical connection with a corresponding signaling device. For exemplary purposes only, for instance, the surface area of the pad members may be at least about 0.5 cm², at least about 1 cm², at least about 2 cm², and, in one embodiment, at least about 3 cm². The pad members are each configured to electrically connect to a signaling device. For instance, when a body fluid is present between the first and second conductive elements, the open circuit between the conductive elements is closed for activating a signaling device attached to the pad members.

The conductive pad members can be made from various different materials depending upon the particular embodiment. For instance, in one embodiment, the pad members comprise a conductive loop-type material. In this embodiment, for instance, the pad members may comprise a conductive nonwoven or a conductive woven material, such as a knitted material. The loop-type material may be made conductive, for instance, by incorporating a conductive material such as carbon into the fibers. Alternatively, the loop-type material may be coated with a conductive material, such as a metal. In still another embodiment, the loop-type material may be made from conductive threads.

When the pad members comprise a loop-type material, the signaling device may include a pair of corresponding terminals that comprise a conductive hook-type material. In this manner, the signaling device may form a hook and loop attachment with the pad members. If the pad members are present on the surface of the chassis, the signaling device may be directly attached to the pad members.

In an alternative embodiment, the pad members may be located below at least one layer of material on the chassis. The material positioned over the pad members may comprise a loop-type material capable of forming a hook and loop attachment with a conductive hook-type material located on the signaling device. The at least one layer of material may also be relatively porous. In this embodiment, the hooks on the signaling device may engage and attach to the layer of material positioned over the pad members. The layer of material, however, may also be sufficiently porous to allow the hooks to penetrate through the material and make an electrical connection with the pad members. In this embodiment, the pad members can be made from any suitable electrically conductive material.

In another alternative embodiment of the present invention, the first and second terminals on the signaling device may be located on a clip device including a pair of opposing plates. The clip device, for instance, may be configured to engage the conductive regions of the absorbent article by clasping over the edge of the article. In particular, the first and second plates may be biased towards each other for engaging an edge of the absorbent article. In one embodiment, for instance, the opposing plates may be pivotally connected together along a hinge. The hinge can include a biasing member, such as a spring, for biasing the two plates towards each other. The first and second terminals can be located on one of the plates or can be located on opposing plates.

When the opposing plates are placed over an edge of the absorbent article, the plates can be configured to apply a clamping force that can assist in making an electrical connection between the first and second terminals on the signaling device and the first and second conductive regions contained in the absorbent article. The first and second terminals, in one embodiment, can each comprise at least one conductive prong that is configured to make an electrical connection with a respective conductive pad member. In one embodiment, the prongs may be configured to penetrate through at least a portion of the chassis in order to make an electrical connection with the first and second conductive pad members. In this embodiment, the pad members can be made from various materials. For instance, in addition to comprising a woven or nonwoven material as described above, the pad members may comprise a film, such as a metal foil or a conductive polymer film such as a conductive mylar film, conductive thread or wire. The pad members may also comprise a conductive ink or adhesive.

Similarly, the at least one prong that comprises the first and second terminals can also vary depending upon the particular embodiment. For instance, in one embodiment, each of the first and second terminals may include a plurality of prongs. The prongs can comprise blade members, teeth members, pin members, hook-like members, and combinations thereof. The plurality of prongs can be arranged on the terminal in a specific pattern, such as in columns and rows, or may be arranged randomly on the terminal. Alternatively, each terminal may also include just a single prong. The prong may comprise, for instance, a blade member or a single pin member.

In still another embodiment of the present invention, each of the pad members are connected to a conductive tab that is present on the surface of the chassis. The signaling device, on the other hand, can include corresponding slots for receiving the conductive tabs and for making an electrical connection between the signaling device and the first and second pad members.

In one embodiment, the chassis may include more than two conductive elements. For instance, the chassis may include a third conductive element that extends into the back region of the chassis and a fourth conductive element that extends into the front region of the chassis. The third conductive element may be connected to a third conductive pad member while the fourth conductive element may be connected to a fourth conductive pad member. Similarly, the signaling device may include four corresponding terminals. In this embodiment, the multiple conductive elements may be used to indicate not only that a body fluid is present, but where the body fluid is located. For instance, if the body fluid is only located in the front region of the chassis, the conductive elements may be configured so that only the circuit between the first conductive element and the fourth conductive element is closed. In this embodiment, the signaling device may be configured to inform the user where the body fluid is positioned.

The signaling device itself may comprise a single unit that attaches to the absorbent article. Alternatively, the signaling device may include a transmitter that attaches to the absorbent article and a receiver that is configured to receive a wireless signal from the transmitter. The receiver, for instance, may indicate to a user that a body fluid has insulted the absorbent article remote from the article itself.

The signaling device may be configured to indicate the presence of a body fluid in various ways. For example, the signaling device may emit a visible alarm and/or an audible alarm. In still another embodiment, the signaling device may be configured to vibrate when a body fluid is sensed.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
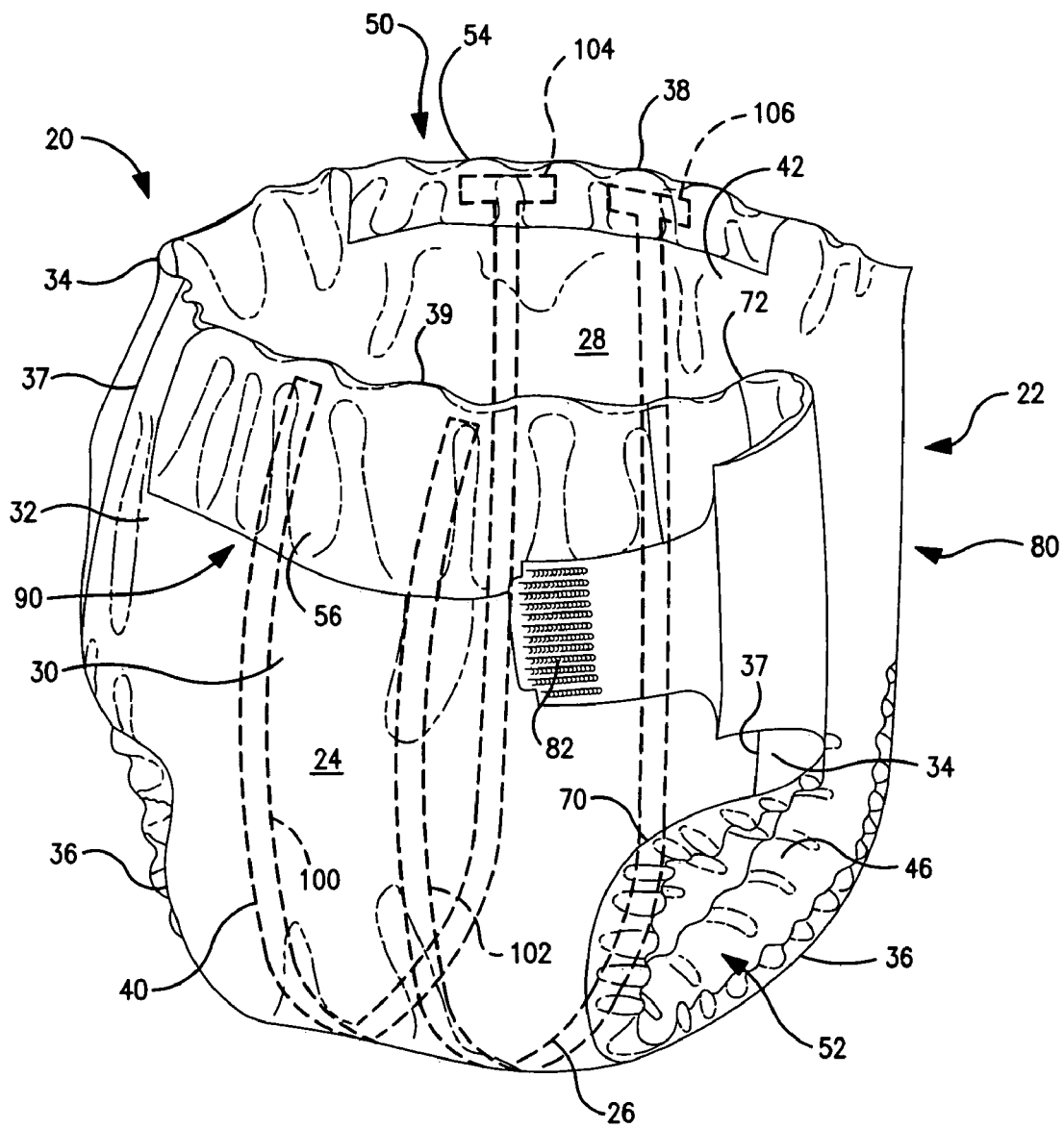
FIG. 1 is a rear perspective view of one embodiment of an absorbent article made in accordance with the present invention.

Repeat use of reference characters in the present specification and drawings is intended to represent the same or analogous features or elements of the present invention.

DETAILED DESCRIPTION OF THE INVENTION

It is to be understood by one of ordinary skill in the art that the present discussion is a description of exemplary embodiments only, and is not intended as limiting the broader aspects of the present invention.

The present disclosure is generally directed to absorbent articles adapted to be attached to a signaling device that may be configured to indicate the presence of a body fluid in the absorbent article or other changes in the condition of the product or wearer. The absorbent article may be, for instance, a diaper, a training pant, an incontinence product, a feminine hygiene product, a medical garment, a bandage, and the like. Absorbent articles made according to the present disclosure include an open circuit that becomes closed when a conductive fluid, such as a body fluid, is sensed in between a pair of conductive leads. Generally, the absorbent articles containing the open circuit are disposable meaning that they are designed to be discarded after a limited use rather than being laundered or otherwise restored for reuse.

The open circuit contained within the absorbent articles of the present disclosure is configured to be attached to a signaling device. The signaling device can provide power to the open circuit while also including some type of audible and/or visible signal that indicates to the user the presence of a body fluid. Although the absorbent article itself is disposable, the signaling device may be reusable from article to article. In this regard, the present disclosure is particularly directed to different types of attachment mechanisms that allow easy connection between the open circuit in the absorbent article and the signaling device. For example, the open circuit contained in the absorbent article may include conductive pad members that have a relatively large surface area in relation to the materials used to construct the remainder of the open circuit. Pad members can be constructed of different materials and can be positioned not only to make an easy connection to the signaling device but also can be incorporated into the absorbent article at the rapid machine speeds that are needed in order to manufacture the articles.

The conductive pad members, for instance, in one embodiment may comprise a conductive loop-type material that is adapted to be connected to a conductive hook-type material disposed on the signaling device or vice versus. Alternatively, the conductive pad members may comprise a conductive film or other similar material and may be engageable by a prong or a conductive tab for connection to the signaling device.

As described above, the open circuit in combination with the signaling device may be configured to indicate the presence of a body fluid contained within the absorbent article. The particular targeted body fluid may vary depending upon the particular type of absorbent article and the desired application. For instance, in one embodiment, the absorbent article comprises a diaper, a training pant, or the like and the signaling device is configured to indicate the presence of urine. Alternatively, the signaling device may be configured to indicate the presence of a metabolite that would indicate the presence of a diaper rash. For adult incontinence products and feminine hygiene products, on the other hand, the signaling device may be configured to indicate the presence of a yeast or of a particular constituent in urine, such as a polysaccharide.

Figure 2:
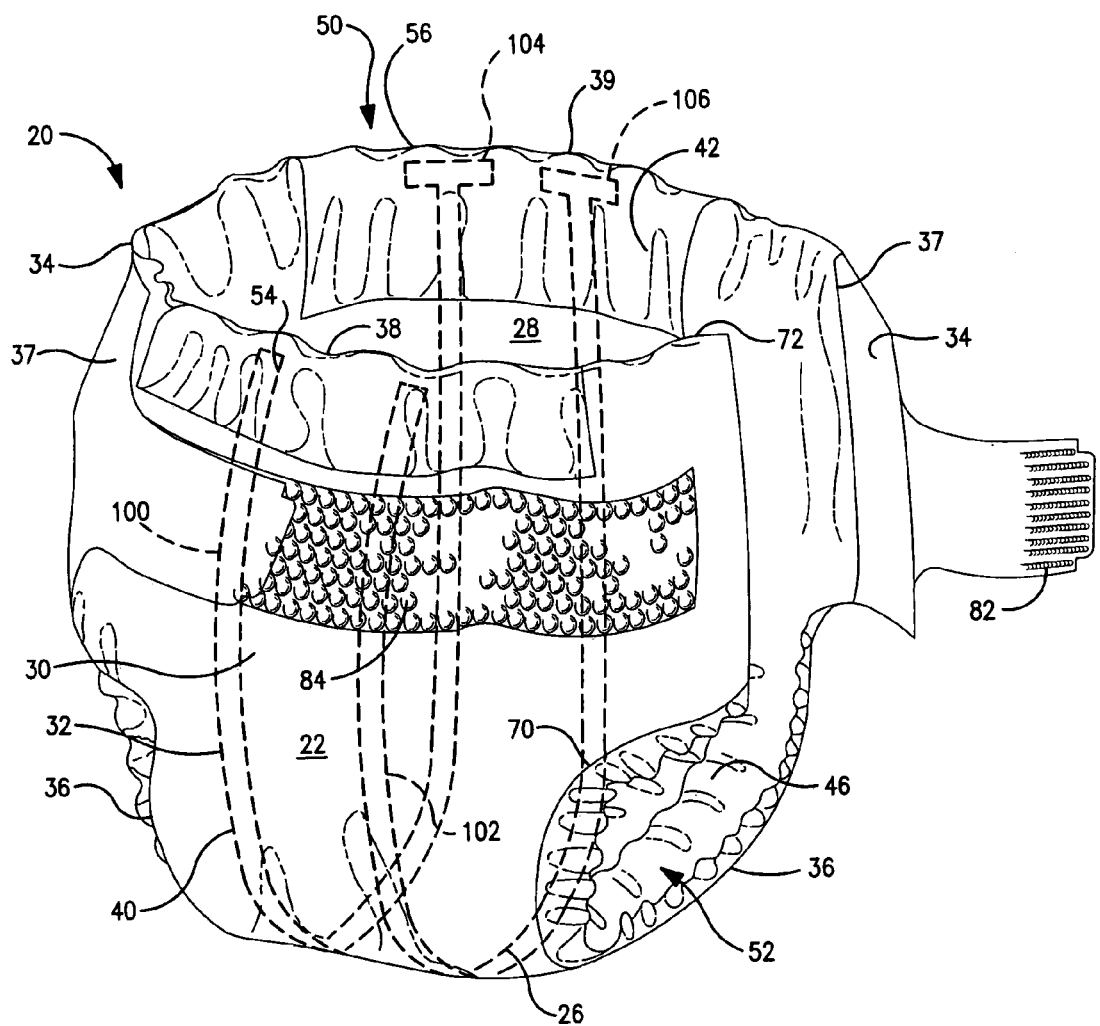
FIG. 2 is a front perspective view of the absorbent article illustrated in FIG. 1.

Referring to FIGS. 1 and 2, for exemplary purposes, an absorbent article 20 that may be made in accordance with the present invention is shown. The absorbent article 20 may or may not be disposable. It is understood that the present invention is suitable for use with various other absorbent articles intended for personal wear, including but not limited to diapers, training pants, swim pants, feminine hygiene products, incontinence products, medical garments, surgical pads and bandages, other personal care or health care garments, and the like without departing from the scope of the present invention.

By way of illustration only, various materials and methods for constructing absorbent articles such as the diaper 20 of the various aspects of the present invention are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

Figure 3:
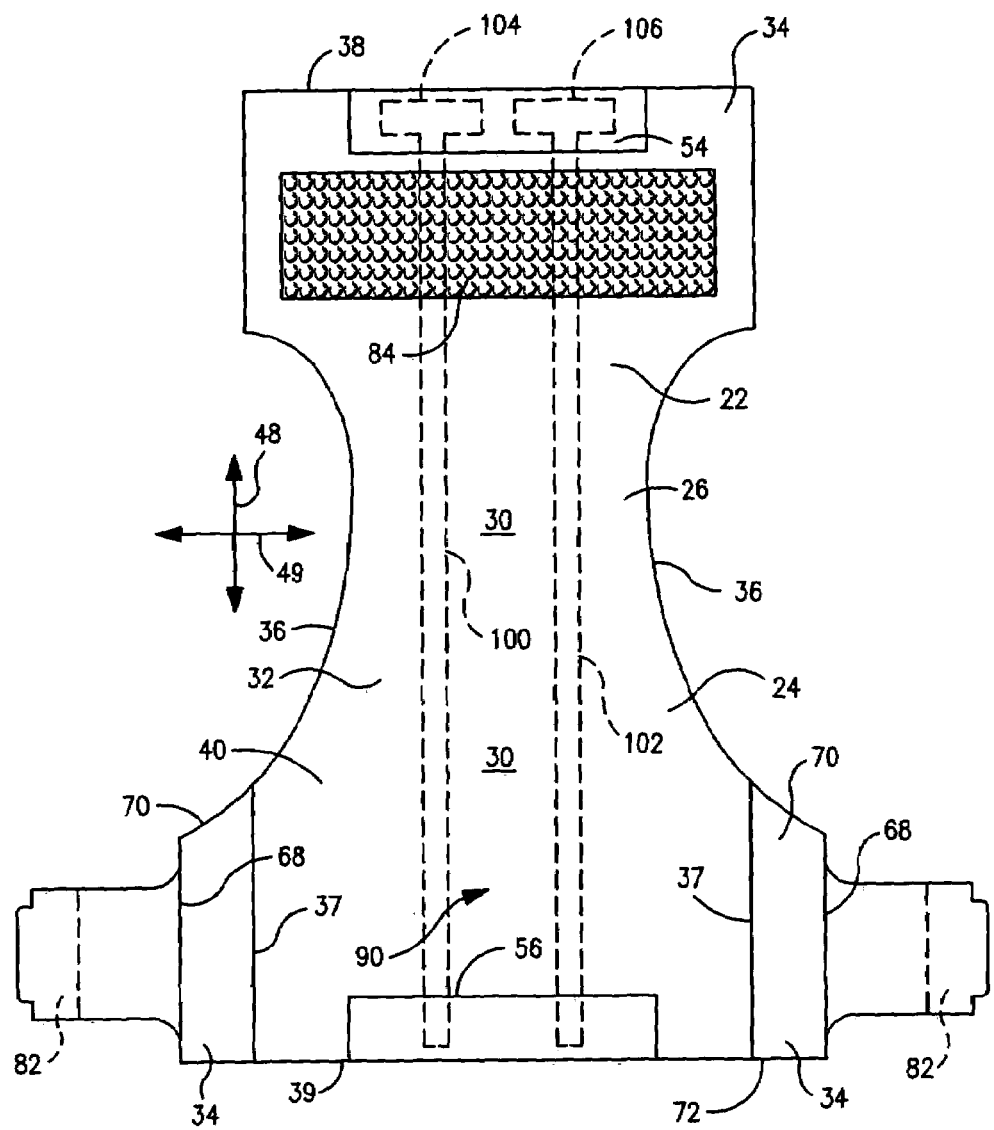
FIG. 3 is a plan view of the absorbent article shown in FIG. 1 with the article in an unfastened, unfolded and laid flat condition showing the surface of the article that faces away from the wearer.
Figure 4:
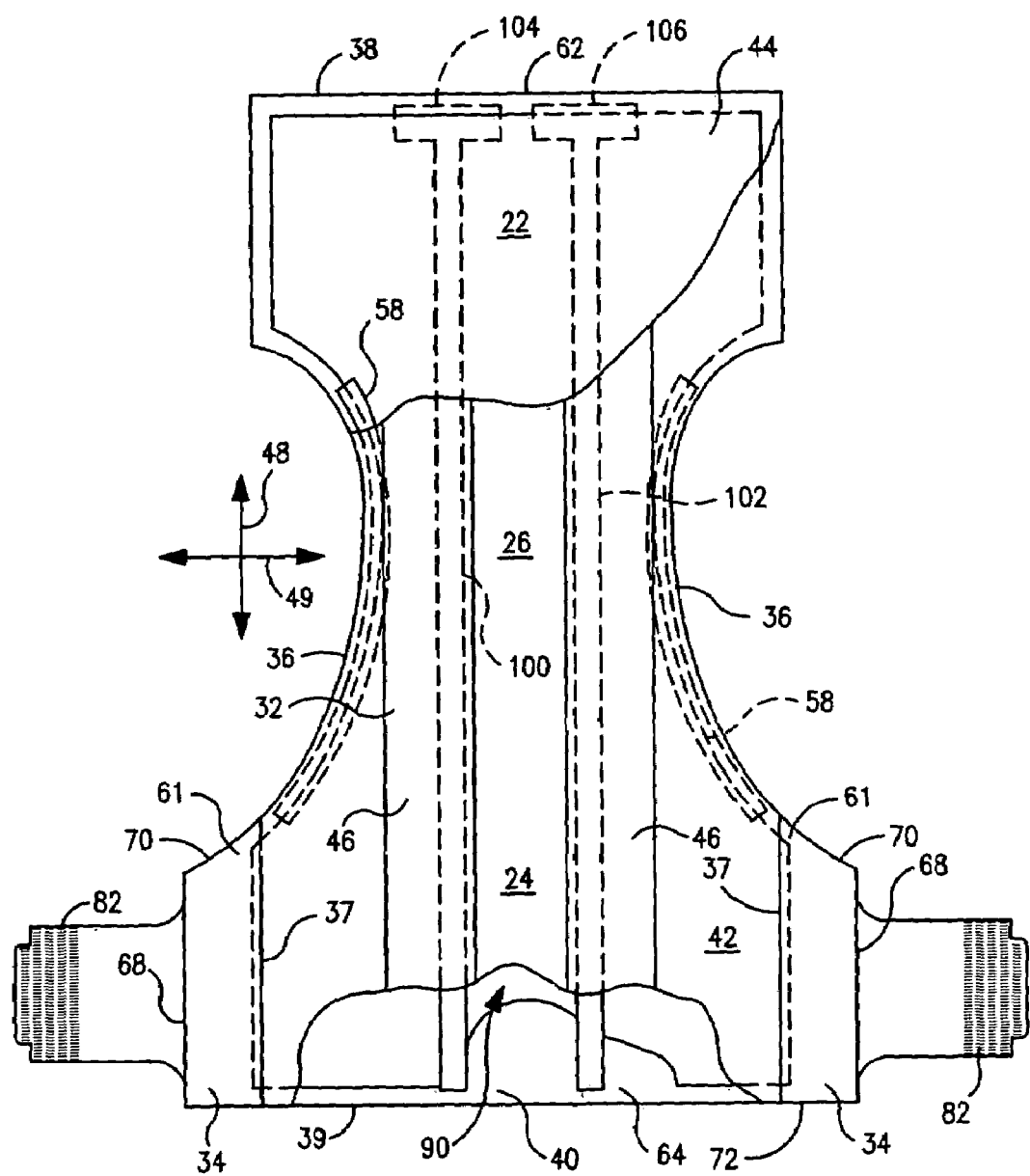
FIG. 4 is a plan view similar to FIG. 3 showing the surface of the absorbent article that faces the wearer when worn and with portions cut away to show underlying features.

A diaper 20 is representatively illustrated in FIG. 1 in a partially fastened condition. The diaper 20 shown in FIGS. 1 and 2 is also represented in FIGS. 3 and 4 in an opened and unfolded state. Specifically, FIG. 3 is a plan view illustrating the exterior side of the diaper 20, while FIG. 4 illustrates the interior side of the diaper 20. As shown in FIGS. 3 and 4, the diaper 20 defines a longitudinal direction 48 that extends from the front of the article when worn to the back of the article. Opposite to the longitudinal direction 48 is a lateral direction 49.

The diaper 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The diaper 20 also defines an inner surface 28 adapted in use (e.g., positioned relative to the other components of the article 20) to be disposed toward the wearer, and an outer surface 30 opposite the inner surface. The front and back regions 22, 24 are those portions of the diaper 20, which when worn, wholly or partially cover or encircle the waist or mid-lower torso of the wearer. The crotch region 26 generally is that portion of the diaper 20 which, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated diaper 20 includes a chassis 32, that, in this embodiment, encompasses the front region 22, the back region 24, and the crotch region 26. Referring to FIGS. 1-4, the chassis 32 includes an outer cover 40 and a bodyside liner 42 (FIGS. 1 and 4) that may be joined to the outer cover 40 in a superimposed relation therewith by adhesives, ultrasonic bonds, thermal bonds or other conventional techniques. Referring to FIG. 4, the liner 42 may suitably be joined to the outer cover 40 along the perimeter of the chassis 32 to form a front waist seam 62 and a back waist seam 64. As shown in FIG. 4, the liner 42 may suitably be joined to the outer cover 40 to form a pair of side seams 61 in the front region 22 and the back region 24. The liner 42 can be generally adapted, i.e., positioned relative to the other components of the article 20, to be disposed toward the wearer's skin during wear of the absorbent article. The chassis 32 may further include an absorbent structure 44 particularly shown in FIG. 4 disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates.

The elasticized containment flaps 46 as shown in FIG. 4 define a partially unattached edge which assumes an upright configuration in at least the crotch region 26 of the diaper 20 to form a seal against the wearer's body. The containment flaps 46 can extend longitudinally along the entire length of the chassis 32 or may extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the diaper 20 may also suitably include leg elastic members 58 (FIG. 4), as are known to those skilled in the art. The leg elastic members 58 can be operatively joined to the outer cover 40 and/or the bodyside liner 42 and positioned in the crotch region 26 of the absorbent article 20.

The leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members 58 may include a plurality of dry-spun coalesced multifilament spandex elastomeric threads sold under the trade name LYCRA and available from Invista, Wilmington, Del., U.S.A.

In some embodiments, the absorbent article 20 may further include a surge management layer (not shown) which may be optionally located adjacent the absorbent structure 44 and attached to various components in the article 20 such as the absorbent structure 44 or the bodyside liner 42 by methods known in the art, such as by using an adhesive. A surge management layer helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. Nos. 5,486,166; and 5,490,846. Other suitable surge management materials are described in U.S. Pat. No. 5,820,973. The entire disclosures of these patents are hereby incorporated by reference herein to the extent they are consistent (i.e., not in conflict) herewith.

As shown in FIGS. 1-4, the absorbent article 20 further includes a pair of opposing elastic side panels 34 that are attached to the back region of the chassis 32. As shown particularly in FIGS. 1 and 2, the side panels 34 may be stretched around the waist and/or hips of a wearer in order to secure the garment in place. As shown in FIGS. 3 and 4, the elastic side panels are attached to the chassis along a pair of opposing longitudinal edges 37. The side panels 34 may be attached or bonded to the chassis 32 using any suitable bonding technique. For instance, the side panels 34 may be joined to the chassis by adhesives, ultrasonic bonds, thermal bonds, or other conventional techniques.

In an alternative embodiment, the elastic side panels may also be integrally formed with the chassis 32. For instance, the side panels 34 may comprise an extension of the bodyside liner 42, of the outer cover 40, or of both the bodyside liner 42 and the outer cover 40.

In the embodiments shown in the figures, the side panels 34 are connected to the back region of the absorbent article 20 and extend over the front region of the article when securing the article in place on a user. It should be understood, however, that the side panels 34 may alternatively be connected to the front region of the article 20 and extend over the back region when the article is donned.

With the absorbent article 20 in the fastened position as partially illustrated in FIGS. 1 and 2, the elastic side panels 34 may be connected by a fastening system 80 to define a 3-dimensional diaper configuration having a waist opening 50 and a pair of leg openings 52. The waist opening 50 of the article 20 is defined by the waist edges 38 and 39 which encircle the waist of the wearer.

In the embodiments shown in the figures, the side panels are releasably attachable to the front region 22 of the article 20 by the fastening system. It should be understood, however, that in other embodiments the side panels may be permanently joined to the chassis 32 at each end. The side panels may be permanently bonded together, for instance, when forming a training pant or absorbent swimwear.

The elastic side panels 34 each have a longitudinal outer edge 68, a leg end edge 70 disposed toward the longitudinal center of the diaper 20, and waist end edges 72 disposed toward a longitudinal end of the absorbent article. The leg end edges 70 of the absorbent article 20 may be suitably curved and/or angled relative to the lateral direction 49 to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present invention. As shown in FIG. 4, the outer edges 68 are generally parallel to the longitudinal direction 48 while the waist end edges 72 are generally parallel to the transverse axis 49. It should be understood, however, that in other embodiments the outer edges 68 and/or the waist edges 72 may be slanted or curved as desired. Ultimately, the side panels 34 are generally aligned with a waist region 90 of the chassis.

The fastening system 80 may include laterally opposite first fastening components 82 adapted for refastenable engagement to corresponding second fastening components 84. In the embodiment shown in the figures, the first fastening component 82 is located on the elastic side panels 34, while the second fastening component 84 is located on the front region 22 of the chassis 32. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the article 20 in its three-dimensional configuration.

The fastening components 82, 84 may be any refastenable fasteners suitable for absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include hook fasteners and the second fastening components 84 include complementary loop fasteners. Alternatively, the first fastening components 82 may include loop fasteners and the second fastening components 84 may be complementary hook fasteners. In another aspect, the fastening components 82, 84 can be interlocking similar surface fasteners, or adhesive and cohesive fastening elements such as an adhesive fastener and an adhesive-receptive landing zone or material; or the like. One skilled in the art will recognize that the shape, density and polymer composition of the hooks and loops may be selected to obtain the desired level of engagement between the fastening components 82, 84. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

In the embodiment shown in the figures, the fastening components 82 are attached to the side panels 34 along the edges 68. In this embodiment, the fastening components 82 are not elastic or extendable. In other embodiments, however, the fastening components may be integral with the side panels 34. For example, the fastening components may be directly attached to the side panels 34 on a surface thereof.

In addition to possibly having elastic side panels, the absorbent article 20 may include various waist elastic members for providing elasticity around the waist opening. For example, as shown in the figures, the absorbent article 20 can include a front waist elastic member 54 and/or a back waist elastic member 56.

As described above, the present disclosure is particularly directed to incorporating a body fluid indicating system, such as a wetness indicating system into the absorbent article 20. In this regard, as shown in FIGS. 1-4, the absorbent article 20 includes a first conductive element 100 spaced from a second conductive element 102. In this embodiment, the conductive elements extend from the front region 22 of the absorbent article to the back region 24 without intersecting. The conductive elements 100 and 102 can comprise any suitable conductive material, such as a conductive thread or a conductive foil. The first conductive element 100 does not intersect the second conductive element 102 in order to form an open circuit that may be closed, for instance, when a conductive fluid is positioned in between the conductive elements. In other embodiments, however, the first conductive element 100 and the second conductive element 102 may be connected to a sensor within the chassis. The sensor may be used to sense changes in temperature or may be used to sense the presence of a particular substance, such as a metabolite.

In the embodiment shown in FIG. 1, the conductive elements 100 and 102 extend the entire length of the absorbent article 20. It should be understood, however, that in other embodiments the conductive elements may extend only to the crotch region 26 or may extend to any particular place in the absorbent article where a body fluid is intended to be sensed.

The conductive elements 100 and 102 may be incorporated into the chassis 32 at any suitable location as long as the conductive elements are positioned so as to contact a body fluid that is absorbed by the absorbent article 20. In this regard, the conductive elements 100 and 102 generally lie inside the outer cover 40. In fact, in one embodiment, the conductive elements 100 and 102 may be attached or laminated to the inside surface of the outer cover 40 that faces the absorbent structure 44. Alternatively, however, the conductive elements 100 and 102 may be positioned on the absorbent structure 44 or positioned on the liner 42.

In order for the conductive elements 100 and 102 to be easily connected to a signaling device, the first conductive element 100 is attached to a first conductive pad member 104, while the second conductive element 102 is connected to a second conductive pad member 106. The pad members 104 and 106 are provided for making a reliable connection between the open circuit formed by the conductive elements to a signaling device that is intended to be installed on the chassis by the consumer. In particular, the pad members 104 and 106 create a target zone for attaching the signaling device and the conductive leads or elements.

In general, the conductive pad members 104 and 106 have a relatively large surface area in relation to the conductive elements 100 and 102. For example, the conductive pad members 104 and 106 may have a surface area of at least 1 $cm^2$, at least 2 $cm^2$, and, in one embodiment, at least 3 $cm^2$. For instance, in one embodiment, the surface area of each pad member may be from about 2 $cm^2$ to about 4 $cm^2$.

The position of the conductive pad members 104 and 106 on the absorbent article 20 can vary depending upon where it is desired to mount the signaling device. For instance, in FIGS. 1, 3 and 4, the conductive pad members 104 and 106 are positioned in the front region 22 along the waist opening of the article. In FIG. 2, on the other hand, the conductive pad members 104 and 106 are positioned in the back region 24 along the waist opening of the article. It should be appreciated, however, that in other embodiments, the absorbent article 20 may include conductive pad members being positioned at each end of each conductive element 100 and 102. In this manner, a user can determine whether or not to install the signaling device on the front or the back of the article. In still other embodiments, it should be understood that the pad members may be located along the side of the article or towards the crotch region of the article.

The position of the conductive pad members 104 and 106 within the multiple layers of the chassis 32 may also vary depending upon where it is desired to connect the signaling device and the type of attachment mechanism used to make a connection with the signaling device. As described above, the pad members 104 and 106 are electrically connected to the conductive elements 100 and 102. Thus, in one embodiment, the pad members 104 and 106 are positioned below at least one layer of the outer cover 40. Positioning the pad members 104 and 106 below at least one layer of material may provide various advantages in some embodiments. For instance, locating the pad members 104 and 106 below at least one layer of material within the chassis 32 protects the pad members during shipping and storage and from forming a short circuit during use especially if the pad members are located adjacent one another. Another benefit to placing the pad members under at least one layer of material is the ability to easily manufacture the absorbent article 20 at high machine speeds.

It should be understood, however, that in other embodiments the conductive pad members 104 and 106 may be positioned at an exterior surface of the chassis 32. For instance, the pad members 104 and 106 may be positioned on the outside surface or on the inside surface as desired.

Figure 5:
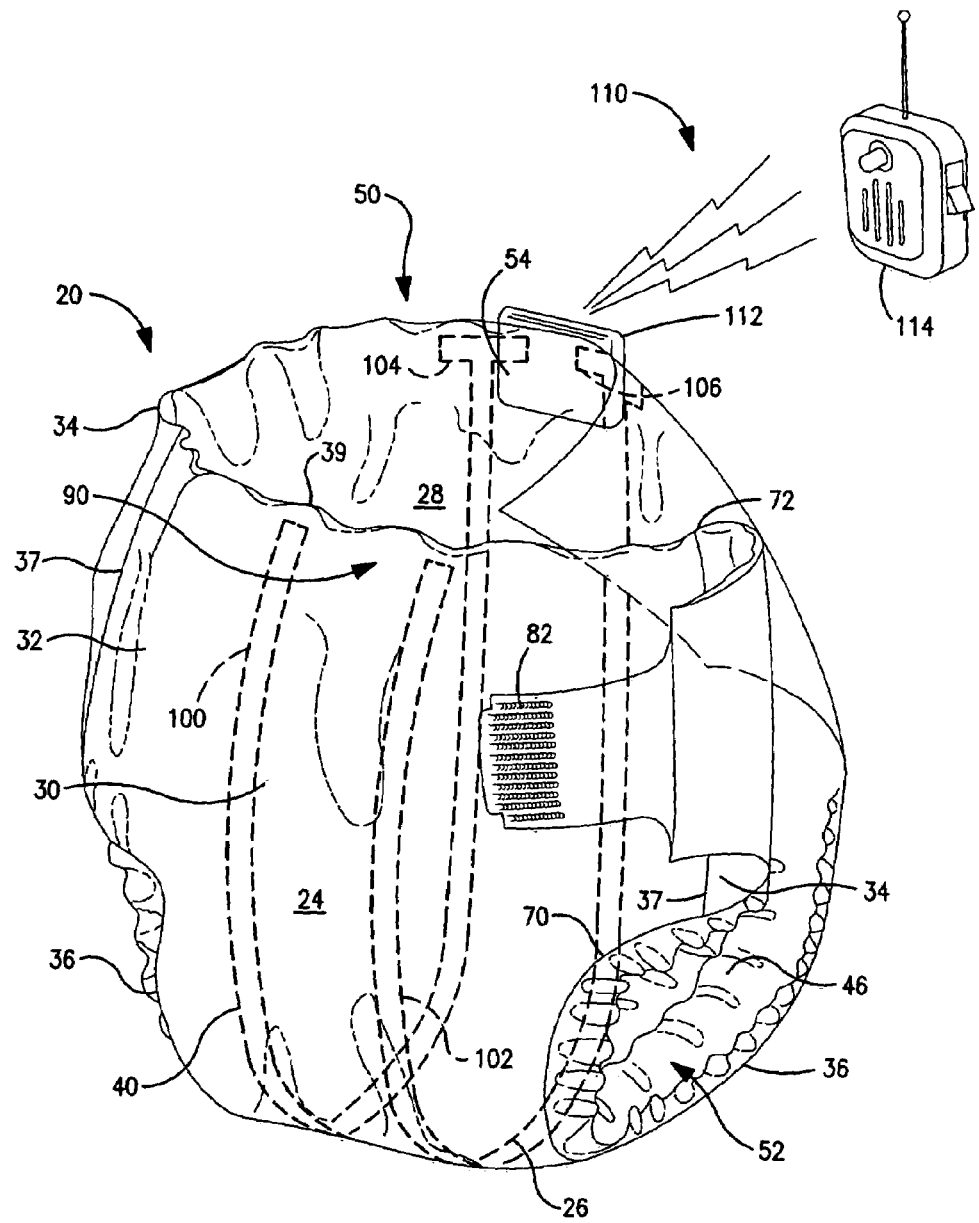
FIG. 5 is a perspective view of the embodiment shown in FIG. 1 further including one embodiment of a signaling device.

Referring to FIG. 5, for exemplary purposes, a signaling device 110 is shown attached to the conductive pad members 104 and 106. As shown, in this embodiment, the signaling device generally 110 includes a transmitter 112 and a receiver 114. The transmitter 112 includes a pair of opposing terminals that are electrically connected to the corresponding conductive pad members. When a body fluid is present in the absorbent article 20, the open circuit formed by the conductive elements 100 and 102 is closed which, in turn, activates the signaling device 110. In particular, in this embodiment, the transmitter 112 sends a wireless signal to the receiver 114 which then indicates to a user that a body fluid is present in the absorbent article.

The signaling device 110 can emit an audible signal or a visual signal in order to indicate to the user that the circuit has been closed. The audible signal, for instance, may be as simple as one or more beeps to perhaps emitting a musical tune. Similarly, if the signaling device 110 issues a visible signal, the visible signal may comprise a few lights or an interactive display. In still another embodiment, the receiver 114 of the signaling device 110 may be configured to vibrate when the circuit within the absorbent article is closed.

As described above, the signaling device 110 can be configured to indicate the presence of any suitable conductive fluid within the absorbent article 20. The fluid may comprise, for instance, urine, a metabolite, and the like.

In the embodiment shown in FIG. 5, the signaling device 110 includes a transmitter 112 in combination with a receiver 114. It should also be understood, however, that the signaling device may comprise a single unit that remains attached to the absorbent article 20. For example, the signaling device may be mounted on the absorbent article and issue a visible signal and/or an audible signal from the article itself.

Figure 7:
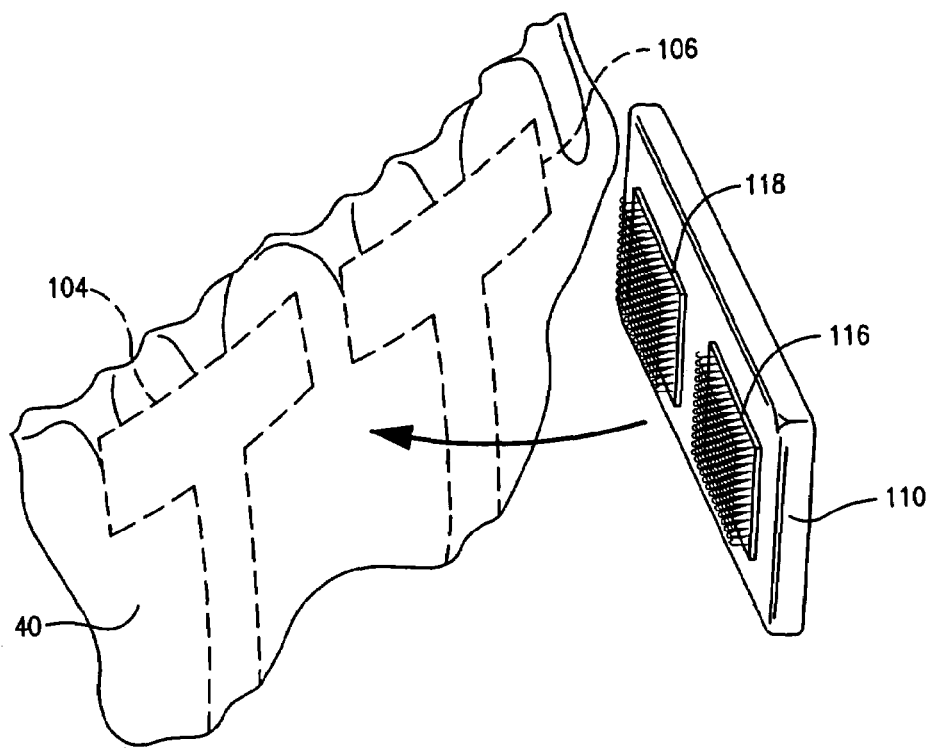
FIG. 7 is a perspective view of one embodiment of an attachment mechanism for a signaling device to the absorbent article in accordance with the present invention.

Different attachment mechanisms between the conductive pad members and the signaling device and the particular construction of the pad member for each embodiment will now be described in detail with respect to FIGS. 7-10. In one embodiment, for instance, as shown in FIG. 7, the pad members 104 and 106 may comprise a conductive loop-type material for making a hook and loop-type connection with the signaling device. For example, as shown, the conductive pad members 104 and 106 comprise a loop-type material, while the signaling device 110 includes corresponding terminals 116 and 118 that comprise a hook-type material. As used herein, a loop-type material refers to any material capable of forming an attachment with a hook-type material. In this embodiment, the conductive pad members 104 and 106 may comprise, for instance, a conductive nonwoven material or a conductive woven material, such as a conductive knitted material. The loop-type material used to form the pad members may be made electrically conductive using various techniques. For instance, in one embodiment, the loop-like material may be made from polymer fibers or filaments that contain a conductive material, such as carbon.

In an alternative embodiment, the loop-type material may be made conductive by incorporating conductive threads, such as metal threads and fibers into the formation of the material. In still other embodiments, the loop-like material may be sputter coated in order to render the material conductive. For instance, the material may be sputter coated with silver or copper. In still other embodiments, the polymers used to form the loop-type material may be doped with a conductive material in any suitable manner in addition to as described above.

The hook-type material used to form the terminals 116 and 118 of the signaling device 110 may also be rendered conductive using any of the above techniques. In one particular embodiment, for instance, each of the hooks contained on the hook-type material may be made from a metal.

Commercially available conductive hook-type material and loop-type material may be obtained, for instance, from Fastech of Jacksonville, Fla., which offers hook and loop tapes that are coated with silver. Other conductive hook and loop materials are available from NC Stat Corporation, from Bio-Logic Systems Corporation and from Velcro Industries B.V.

In this embodiment, the conductive pad members 104 and 106 may be present at the surface of the absorbent article for making a connection with the signaling device. Alternatively, the conductive pad members 104 and 106 may be present below the surface. In this embodiment, an opening may be made in the overlying material in order to make a connection. Alternatively, the overlying material may include perforations or be sufficiently porous for a hook and loop attachment to be made through the material.

Figure 8:
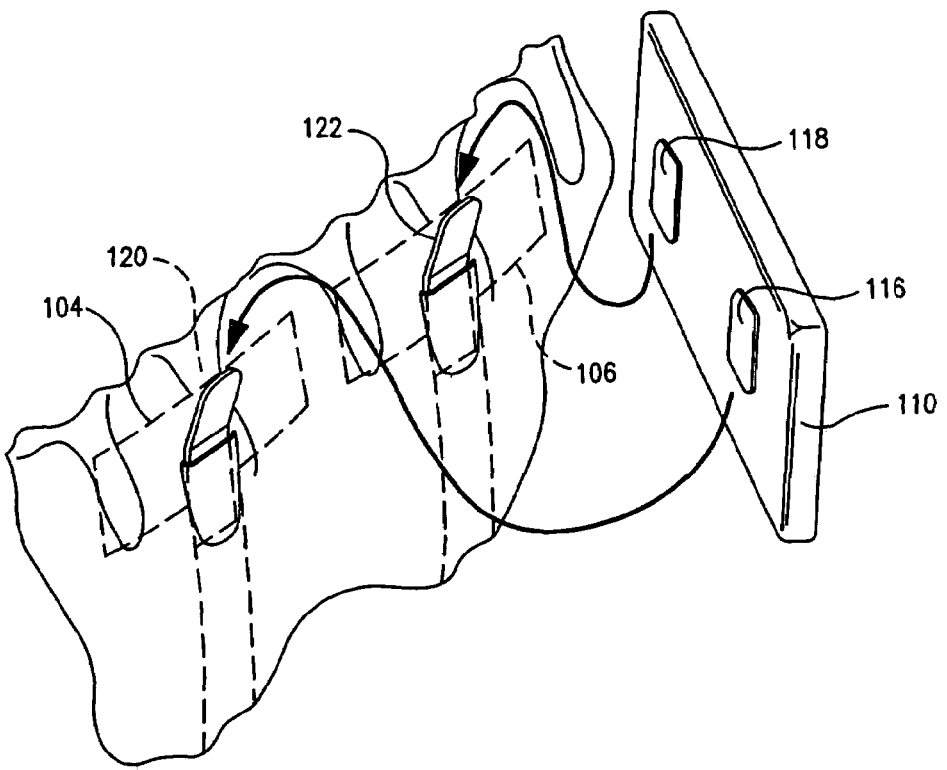
FIG. 8 is another embodiment of an attachment mechanism for attaching a signaling device to an absorbent article in accordance with the present invention.

Referring to FIG. 8, another embodiment of an attachment mechanism for attaching the conductive pad members 104 and 106 to the terminals 116 and 118 on the signaling device 110 is shown. In this embodiment, the pad members 104 and 106 are electrically connected to corresponding conductive tab members 120 and 122. As illustrated, the first terminal 116 and the second terminal 118 on the signaling device 110 comprise corresponding slots or pockets that are configured to receive the conductive tab members 120 and 122. In this manner, electrical connection is made between the signaling device 110 and the pad members 104 and 106.

In the embodiment shown in FIG. 8, the conductive pad members 104 and 106 are illustrated embedded within the chassis 32. In particular, the pad members 104 and 106 are located below at least one layer of material. The corresponding conductive tab members 120 and 122, however, penetrate the outer layers to make an electrical contact with the pad members.

In the embodiment illustrated in FIG. 8, the conductive pad members 104 and 106 can be made from various materials. For instance, the pad members 104 and 106 can be made from any of the materials described above with respect to the embodiment illustrated in FIG. 7. Alternatively, the pad members may comprise other conductive woven or nonwoven fabrics that may not be suitable as a loop-type material.

In addition to woven and nonwoven fabrics, the pad members 104 and 106 as shown in FIG. 8 may also comprise a conductive film. For instance, the pad members may comprise a metal foil or an otherwise conductive film. In one particular embodiment, for instance, the pad members may comprise a conductive mylar film. In an alternative embodiment, the pad members may comprise a conductive ink printed on a layer of material that forms the chassis or a conductive adhesive applied to one of the materials that comprises the chassis.

In still another embodiment of the present invention, the conductive pad members may be embedded within the chassis 32 as shown in FIG. 8. Specifically, the conductive pad members may lie below at least one layer of material. The material covering the pad members may comprise a suitable loop-type material for making a hook and loop attachment.

For example, in one embodiment, the overlying layer of material may comprise a nonwoven web, such as a spunbond web.

In this embodiment, the signaling device may include conductive terminals that comprise a hook-type material as shown in FIG. 7. The hook-type terminals may be configured to attach to the layer of material that covers the pad members. The layer of material, however, may be sufficiently porous to allow the individual hooks not only to engage the layer but also to penetrate through the layer and make an electrical connection with the conductive pad members. Thus, in this embodiment, the terminals on the signaling device attach to a nonconductive layer in a manner that still provides an electrical connection with the conductive pad members.

Figure 9:
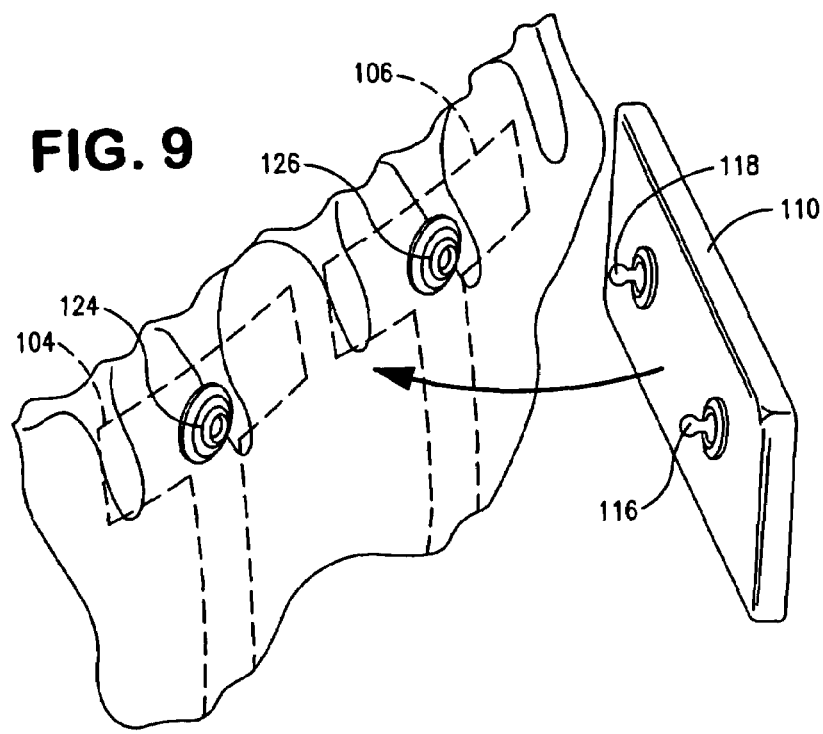
FIG. 9 is still another embodiment of an attachment mechanism for attaching a signaling device to an absorbent article in accordance with the present invention.

Referring to FIG. 9, still another embodiment of an attachment mechanism in accordance with the present invention is shown. In this embodiment, each of the conductive pad members 104 and 102 are electrically connected to a prong receiving member 124 and 126 respectively. As shown, the signaling device 110 includes corresponding prongs 116 and 118 that serve as the first and second terminals. The prongs 116 and 118 are configured to snap in place into the prong receiving members 124 and 126.

In one embodiment, the prong receiving members 124 and 126 may be located below one or more layers of material. The prongs 116 and 118 disposed on the signaling device 110, on the other hand, are configured to pierce the overlying layers of material in order to form an electrical connection with the prong receiving members.

Alternatively, openings may be formed in the overlying material so that the prongs 116 and 118 may be inserted through the openings in the overlying material and engage the prong receiving members 124 and 126. It should be understood that, in the embodiment illustrated in FIG. 9, the prong receiving members and the prongs may have any suitable shape in order to attach together. For example, the present disclosure is intended to cover any suitable male-female connections.

Figure 10:
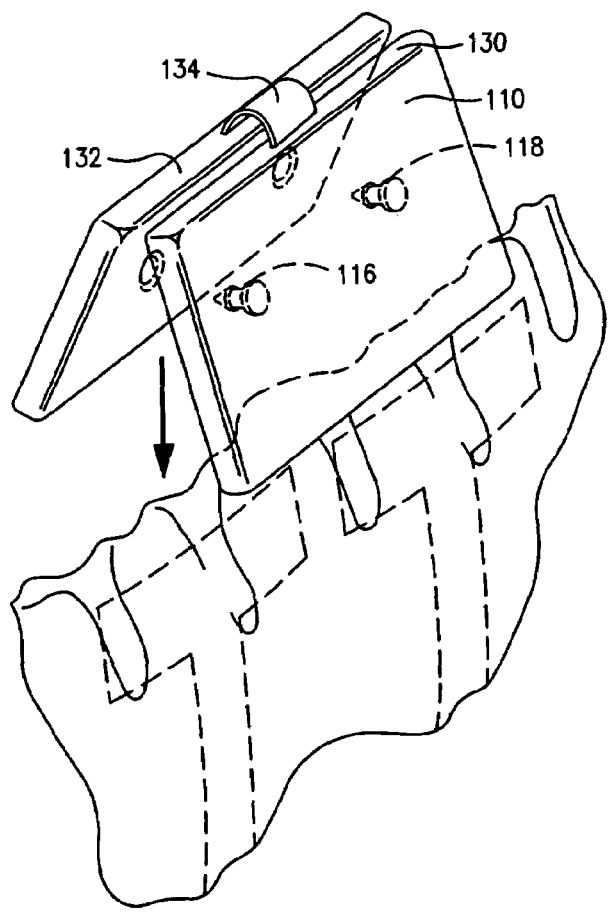
FIG. 10 is a perspective view of another embodiment of an attachment mechanism for attaching a signaling device to an absorbent article in accordance with the present invention.

Referring to FIG. 10, another embodiment of an attachment mechanism that may be used to attach a signaling device to the open circuit contained in the absorbent article is shown. In this embodiment, the signaling device 110 comprises a clip device including a first plate 130 spaced from a second plate 132. More particularly, an end of the first plate 130 is pivotally connected to an end of the second plate 132 about a hinge 134.

In order to make an electrical connection with the conductive pad members 104 and 106, the first plate 130 includes a pair of prongs that serve as the first terminal 116 and the second terminal 118.

As shown in the drawing, the plates 130 and 132 of the signaling device 110 are configured to be placed over an edge of the chassis and brought together such that the prongs 116 and 118 pierce the chassis and lock into place. Specifically, the prongs 116 and 118 are intended to pierce the chassis where the pad members 104 and 106 are located in order to make an electrical connection with the pad members. This embodiment provides various advantages and benefits. In particular, in this embodiment, the pad members 104 and 106 can be located at any position within the chassis and still be contacted with the prongs 116 and 118. In this embodiment, the prongs 116 and 118 can pierce through the entire thickness of the chassis or may only partially penetrate the chassis in order to make a connection with the pad members 104 and 106.

Referring to FIGS. 11 through 16, other embodiments of various clip devices that may be used as a signaling device are illustrated. Like reference numerals have been used to indicate the same or similar elements.

Figure 11:
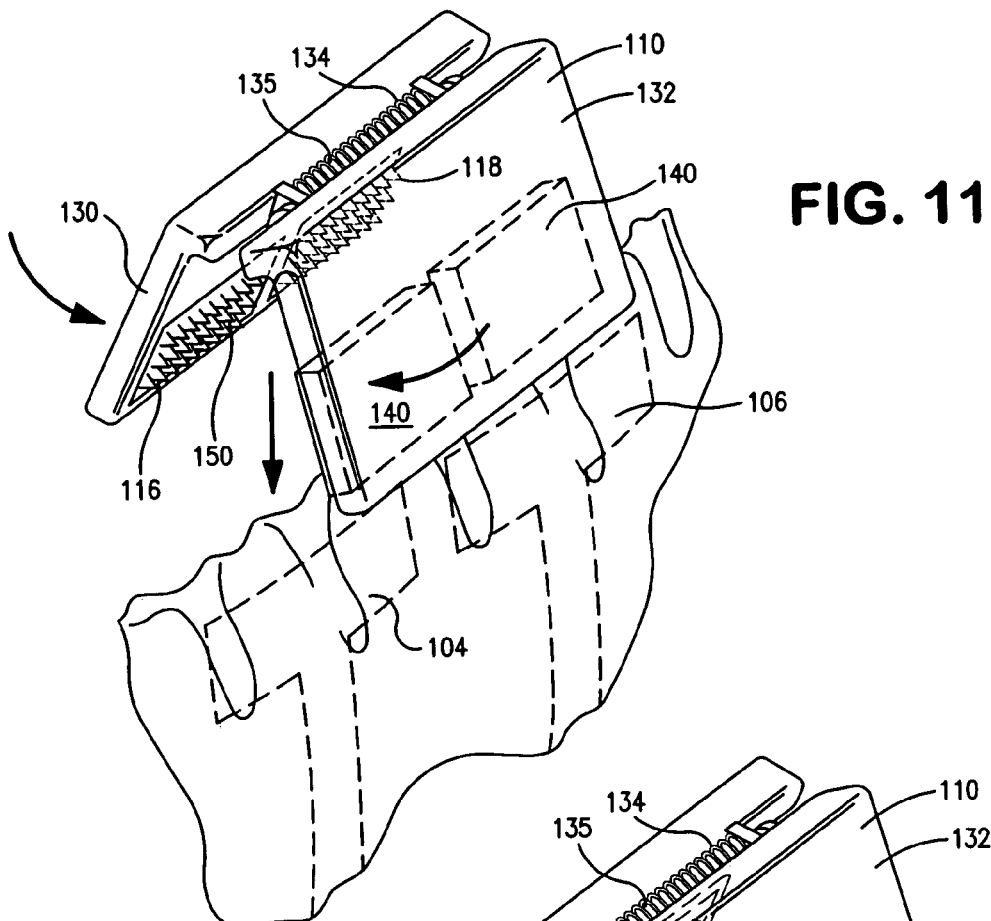
FIG. 11 is a perspective view of another embodiment of an attachment mechanism for attaching a signaling device to an absorbent article in accordance with the present invention.

Referring to FIG. 11, for instance, a signaling device 110 is shown that comprises a clip device including a first plate 130 spaced from a second plate 132. The plates 130 and 132 are biased towards each other by a spring 135 positioned about a hinge 134. The signaling device 110 is designed to be placed over an edge of an absorbent article in accordance with the present disclosure.

More particularly, the signaling device 110 includes a first terminal 116 and a second terminal 118 positioned on the first plate 130. The terminals are configured to make an electrical connection with a first conductive pad member 104 and a second conductive pad member 106 that are located within the absorbent article. In order to assist in making the connection, each of the terminals include a plurality of prongs 150. In this embodiment, the prongs 150 comprise pointed teeth that are configured to not only hold the signaling device in position but also to penetrate the chassis if necessary and make an electrical connection with the pad members 104 and 106. As shown, in this embodiment, the terminals 116 and 118 include rows of teeth 150. It should be understood, however, that more or less teeth may be present on the terminals and may be positioned according to any suitable pattern.

If desired, the second plate 132 may further include one or more backing members 140. The backing members are positioned on the plate 132 so as to be located opposite the teeth 150. The backing members 140 can be made of any suitable material capable of receiving the teeth 150 should the teeth extend all the way through the chassis. The backing members 140, for instance, can be made from any suitable elastomeric material, foam material or polymeric material.

Figure 12:
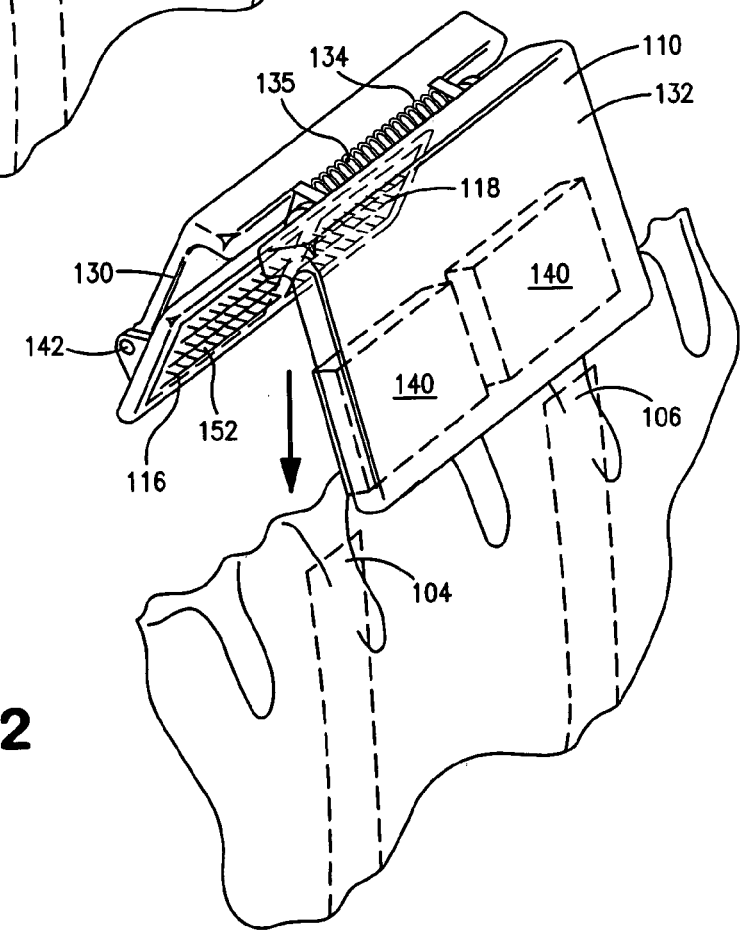
FIG. 12 is a perspective view of still another embodiment of an attachment mechanism for attaching a signaling device to an absorbent article in accordance with the present invention.

Referring to FIG. 12, another embodiment of a signaling device 110 is illustrated including a clip device as shown in FIG. 11. In the embodiment shown in FIG. 12, however, instead of teeth, the terminals 116 and 118 include a plurality of blades 152 having a generally rectangular shape. The blades 152 are for making an electrical connection with the pad members 104 and 106. As shown, in this embodiment, the pad members 104 and 106 have an "I" shape instead of a "T" shape as shown in FIG. 11. The blades 152 can also be configured to partially penetrate through the chassis in order to make the electrical connection.

In the embodiment illustrated in FIG. 12, the terminals 116 and 118 are also pivotally connected to the plate 130 about a pivot pin 142. It may be desirable in some applications to make the terminals pivot with respect to the plate 130 so as to facilitate positioning of the terminals when placed on an absorbent article.

Figure 13:
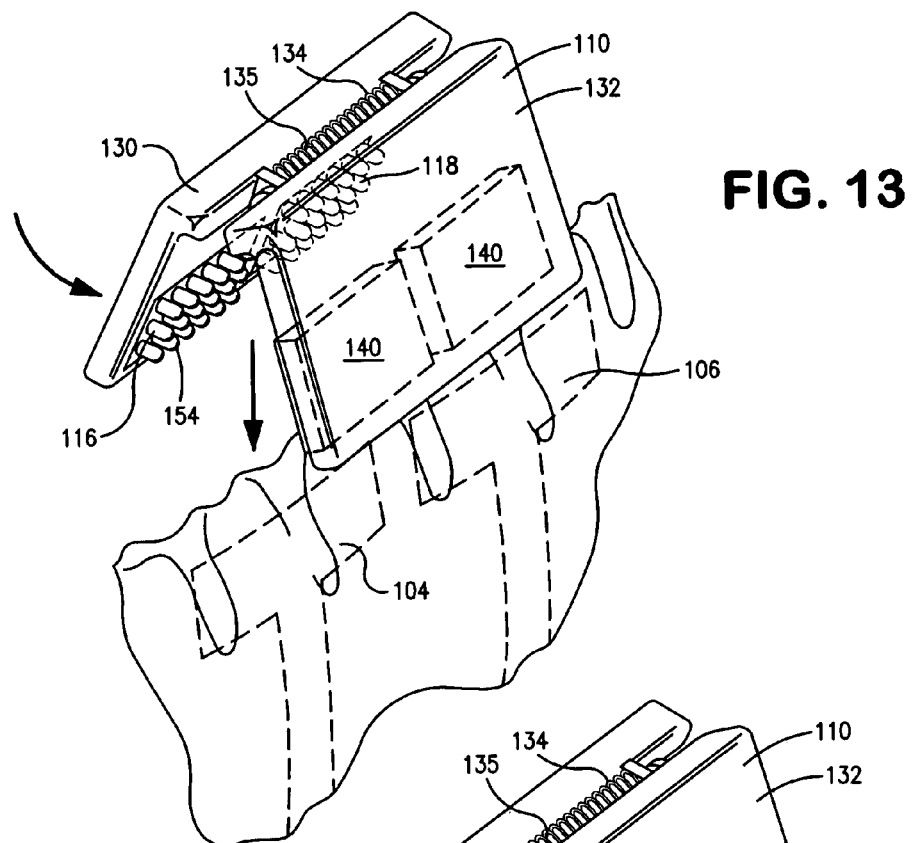
FIG. 13 is a perspective view of yet another embodiment of an attachment mechanism for attaching a signaling device to an absorbent article in accordance with the present invention.

Referring to FIG. 13, still another embodiment of a signaling device 110 comprising a clip device is illustrated. The embodiment shown in FIG. 13 is very similar to the embodiment shown in FIG. 11. Instead of including teeth to comprise the terminals, however, in the embodiment illustrated in FIG. 13, the terminal 116 and the terminal 118 include a plurality of pin members 154. The pin members 154 can have any suitable shape and can be made from any suitable conductive material capable of forming an electrical connection with the conductive pad members 104 and 106. In the embodiment illustrated in FIG. 13, the pin members 154 have a rounded shape. It should be understood, however, that in other embodiments, the pin members may have a more pointed shape. Further, more or less pin members may be present on the terminal 116 as desired.

Figure 14:
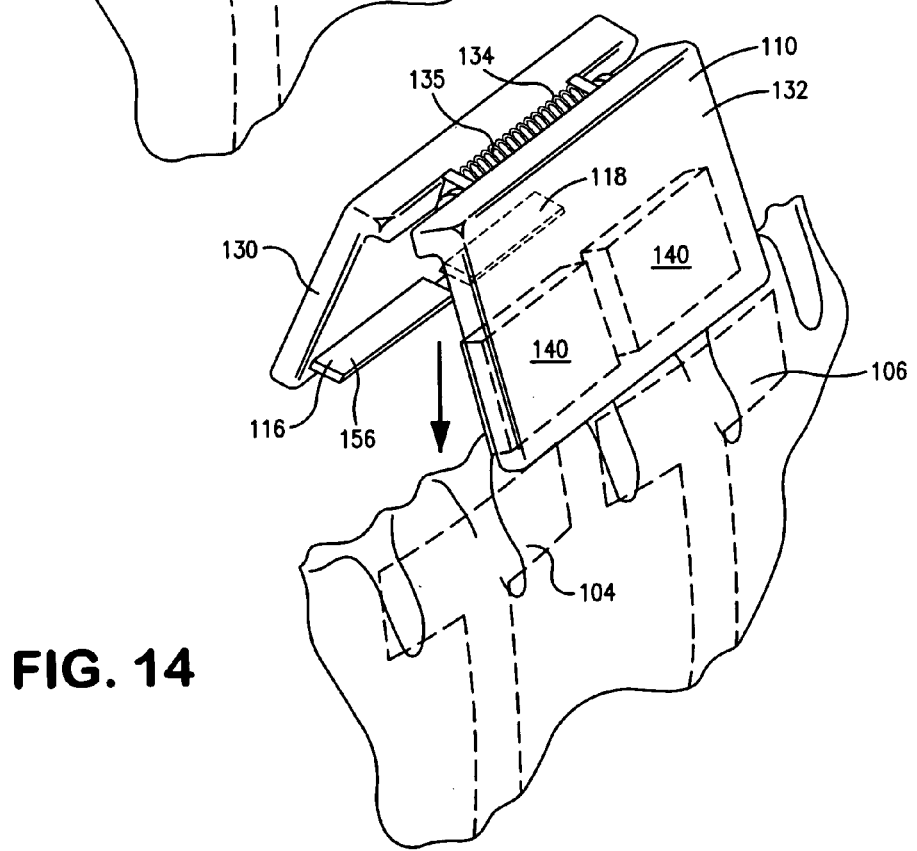
FIG. 14 is a perspective view of another embodiment of an attachment mechanism for attaching a signaling device to an absorbent article in accordance with the present invention.

Referring to FIG. 14, still another embodiment of a signaling device comprising a clip device is illustrated. In this embodiment, the first terminal 116 and the second terminal 118 include a single prong that is in the shape of a blade 156.

The blade 156 can extend the entire length of the terminal and can generally have about the same length as the corresponding pad member 104 and 106.

When the terminals include only a single prong member, it should be understood that the prong can also comprise a single tooth or a single pin member as shown in FIG. 10.

Figure 15:
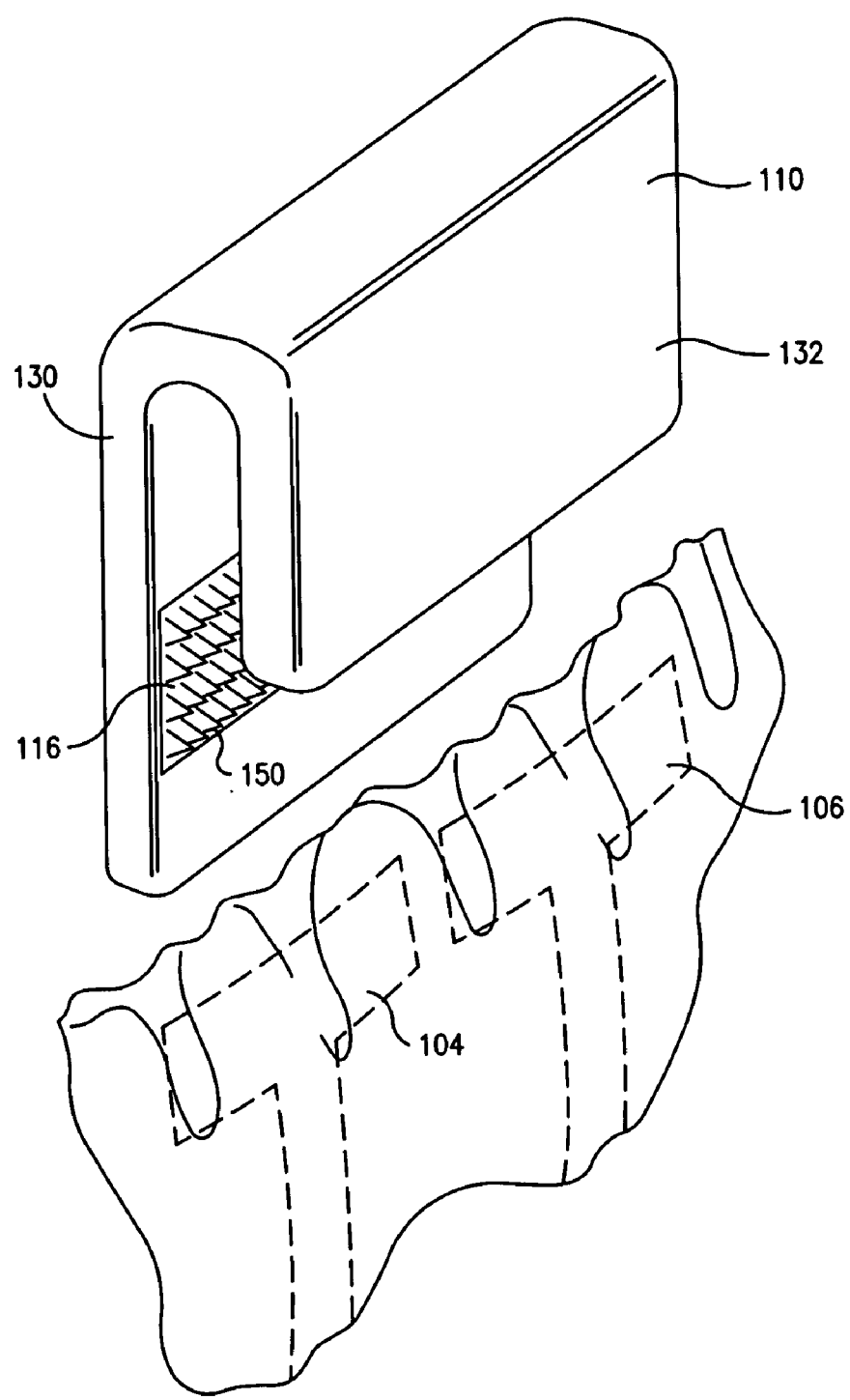
FIG. 15 is a perspective view of another embodiment of an attachment mechanism for attaching a signaling device to an absorbent article in accordance with the present invention.

Referring to FIG. 15, still another embodiment of a signaling device 110 is shown. In this embodiment, the signaling device 110 includes a clip device comprising a first plate 132 spaced from a second plate 130. The plates 132 and 130 are integral with each other and are made from a flexible material that allows the plates to be separated from each other for placing the signaling device over an edge on an absorbent article. Once the plates, however, are placed on the absorbent article, the plates are biased towards each other for holding the signaling device in place. In this manner, the signaling device 110 has a paper clip-like structure.

In the embodiment illustrated in FIG. 15, the signaling device 110 can be made from any suitable material. For example, in one embodiment, the signaling device can be made from a flexible plastic material. It should be understood, however, that elastomeric materials and metal materials may also be used.

Similar to the embodiment shown in FIG. 11, the signaling device 110 includes a first terminal 116 and a second terminal (not shown). The first terminal 116 is comprised of a plurality of teeth 150 that are intended to make an electrical connection with a corresponding pad member 104.

Figure 16:
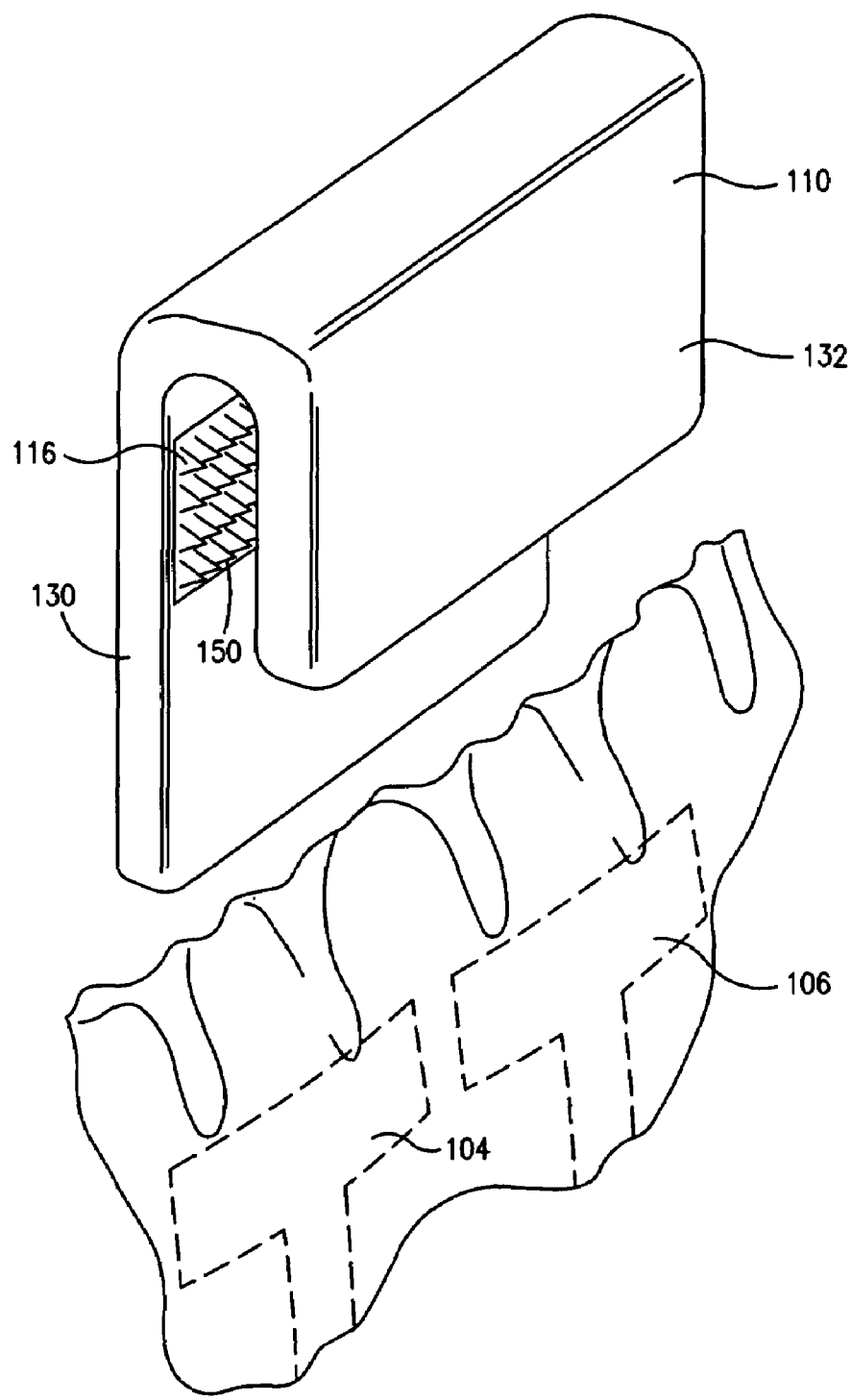
FIG. 16 is a perspective view of still another embodiment of an attachment mechanism for attaching a signaling device to an absorbent article in accordance with the present invention.

Referring to FIG. 16, still another embodiment of a signaling device 110 made in accordance with the present disclosure is illustrated. The signaling device 110 as shown in FIG. 16 is very similar to the signaling device shown in FIG. 15. In the embodiment shown in FIG. 16, however, the first terminal 116 is positioned lower on the plate 130. Likewise, the conductive pad members 104 and 106 are positioned farther down on the absorbent article. In this manner, the conductive pad members 104 and 106 and the corresponding terminals on the signaling device may be positioned below an elastic waistband that may be incorporated into the absorbent article. Thus, the signaling device can connect to the open circuit in the article without the elastic waistband interfering with the connection. Similarly, an elastic waistband if incorporated into the absorbent article in the embodiment shown in FIG. 15 may be placed below the conductive pad members 104 and 106.

Figure 6:
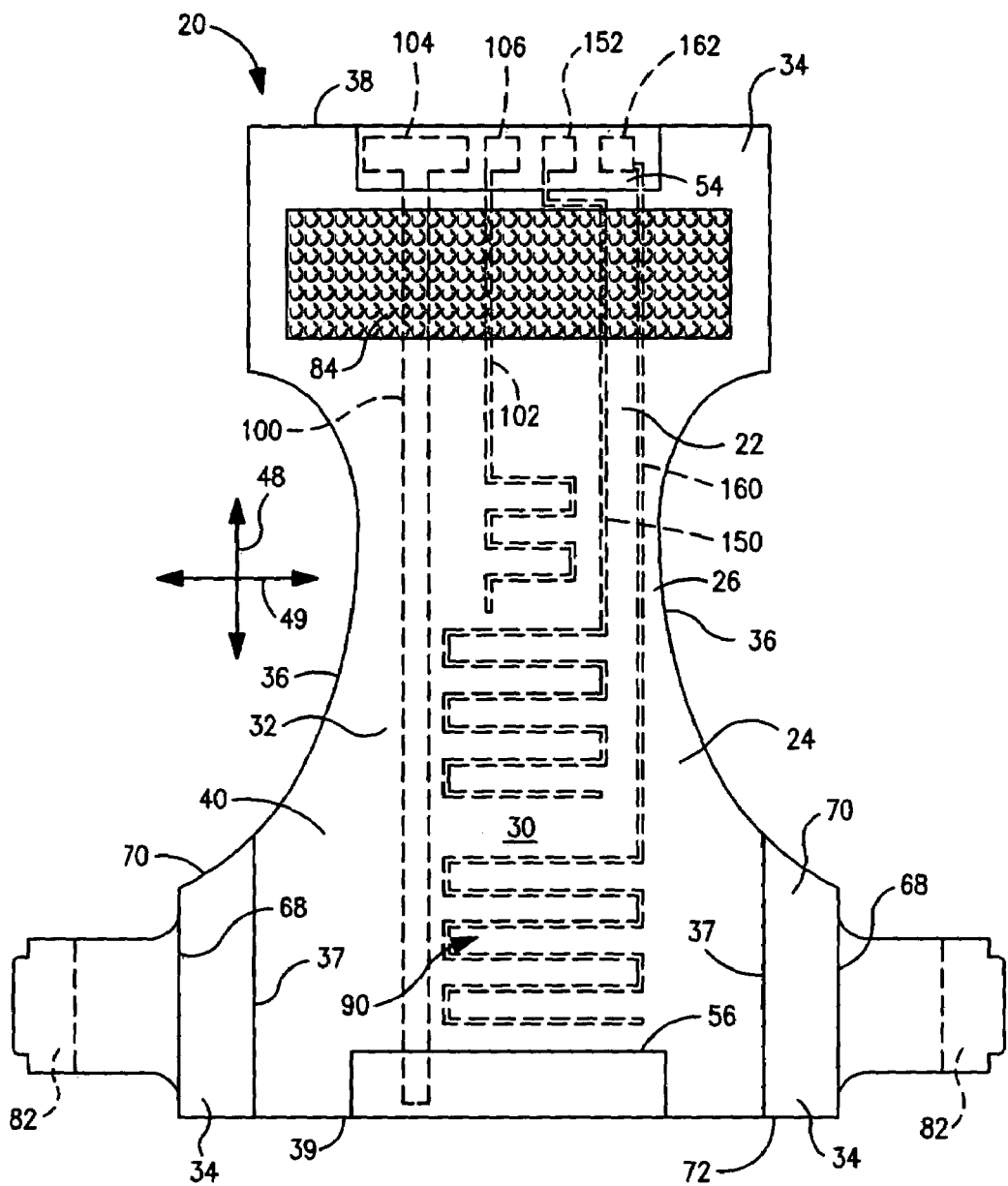
FIG. 6 is a plan view of another embodiment of an absorbent article made in accordance with the present invention illustrating the article in an unfastened, unfolded and laid flat condition illustrating the surface of the article that faces away from the wearer.

Referring to FIG. 6, still another embodiment of an absorbent assembly 20 made in accordance with the present invention is shown. Like reference numerals have been used to indicate similar elements. In the embodiment illustrated in FIG. 6, in addition to the first conductive element 100 and the second conductive element 102, the absorbent article includes a third conductive element 150 and a fourth conductive element 160. As illustrated, the first conductive element 100 extends the entire length of the absorbent article. The second conductive element 102, however, is located primarily within the front region of the chassis. The third conductive element 150 passes through the front region and is primarily located in the crotch region of the chassis. In particular, as shown, in the crotch region the third conductive element 150 forms a labrythine path.

Finally, the fourth conductive element 160 extends through the front region and the crotch region and then is primarily located in the back region of the chassis. Again, in the back region, the fourth conductive element 160 forms a labrythine path.

Similar to the conductive elements 100 and 102, the third conductive element 150 is connected to a third conductive pad member 152, while the fourth conductive element 160 is connected to a fourth conductive pad member 162.

In the embodiment illustrated in FIG. 6, the additional conductive elements are used for not only indicating the presence of a body fluid but also indicating the location of the body fluid. For instance, if the body fluid is located in the front region, the open circuit between the first conductive element 100 and the second conductive element 102 is closed. If the body fluid is contained in the crotch region, on the other hand, the electric circuit formed between the third conductive element 150 and the first conductive element 100 becomes closed. In similar fashion, if the body fluid is located in the back region, the circuit becomes closed between the fourth conductive element 160 and the first conductive element 100.

The embodiment illustrated in FIG. 6 is intended to be placed in conjunction with a signaling device that includes four corresponding terminals for each of the four conductive pad members. The signaling device can then be configured to not only indicate when a body fluid is present but also indicate which circuits are closed, thus indicating the location of the body fluid in addition to its mere presence.

The remaining materials used to form the absorbent article 20 that surround the waist elastic members 54 and 56 may vary depending upon the particular application and the particular product being produced.

The outer cover 40, for instance, may be breathable and/or may be liquid impermeable. The outer cover 40 may be constructed of a single layer, multiple layers, laminates, spunbond fabrics, films, meltblown fabrics, elastic netting, microporous webs, bonded card webs or foams provided by elastomeric or polymeric materials. The outer cover 40, for instance, can be a single layer of a liquid impermeable material, or alternatively can be a multi-layered laminate structure in which at least one of the layers is liquid impermeable. In other embodiments, however, it should be understood that the outer cover may be liquid permeable. In this embodiment, for instance, the absorbent article may contain an interior liquid barrier layer.

For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Bostik Findley Adhesives, Inc., of Wauwatosa, Wis., U.S.A., or from National Starch and Chemical Company, Bridgewater, N.J. U.S.A. The liquid permeable outer layer can be any suitable material and is desirably one that provides a generally cloth-like texture. One example of such a material is a 20 gsm (grams per square meter) spunbond polypropylene nonwoven web. The outer layer may also be made of those materials of which the liquid permeable bodyside liner 42 is made.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumburg, Ill., U.S.A.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. A suitable bodyside liner 42 may be manufactured from a wide selection of web materials, such as porous foams, reticulated foams, apertured plastic films, woven and non-woven webs, or a combination of any such materials. For example, the bodyside liner 42 may include a meltblown web, a spunbonded web, or a bonded-carded-web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity.

The absorbent structure 44 may be disposed between the outer cover 40 and the bodyside liner 42. The absorbent structure 44 can be any structure or combination of components which are generally compressible, conformable, non-irritating to a wearer's skin, and capable of absorbing and retaining liquids and certain body wastes. For example, the absorbent structure 44 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular aspect, the absorbent web material is a matrix of cellulosic fluff and superabsorbent hydrogel-forming particles. The cellulosic fluff may include a blend of wood pulp fluff. One preferred type of fluff is identified with the trade designation CR 1654, available from Bowater of Greenville, S.C., USA, and is a bleached, highly absorbent sulfate wood pulp containing primarily southern soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art. Furthermore, the absorbent structure may itself encompass multiple layers in the Z direction. Such multiple layers may take advantage of differences in absorbency capacity, such as by placing a lower capacity absorbent material layer closer to the liner 42 and a higher capacity absorbent material closer to the outer cover layer 40. Likewise, discrete portions of an absorbent single-layered structure may encompass higher capacity absorbents, and other discrete portions of the structure may encompass lower capacity absorbents.

As a general rule, the superabsorbent material is present in the absorbent web in an amount of from about 0 to about 90 weight percent based on total weight of the web. The web may have a density within the range of about 0.10 to about 0.60 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and desirably is capable of absorbing more than about 25 times its weight in liquid. Suitable superabsorbent materials are readily available from various suppliers. For example, SXM 9394, and Favor 9543 superabsorbents are available from DeGussa Superabsorbers.

After being formed or cut into a desired shape, the absorbent web material may be wrapped or encompassed by a suitable tissue or meltblown web or the like wrap sheet that aids in maintaining the integrity and shape of the absorbent structure 44.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference to the extent they are consistent (i.e., not in conflict) herewith.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. An absorbent article comprising:
    a chassis comprising an outer cover having an interior surface and an exterior surface and an absorbent structure positioned adjacent the interior surface of the outer cover, the chassis including a crotch region positioned in between a front region and a back region, the front region and the back region defining a waist region therebetween;
    first and second conductive elements contained in the chassis, the conductive elements extending from the waist region to the crotch region without intersecting, the first and second conductive elements forming part of a circuit that is configured to sense the presence of a substance;
    a first conductive pad member electrically connected to the first conductive element and a second conductive pad member electrically connected to the second conductive element, each of the conductive pad members being positioned below at least one layer of material of the chassis; and
    a signaling device that is intended to connect to the first conductive pad member and to the second conductive pad member, the signaling device comprising a clip member including a first terminal and a second terminal, each terminal comprising at least one prong, wherein the at least one layer of material of the chassis is sufficiently porous for the prongs to connect through the material to the first conductive pad member and the second conductive pad member respectively.

2. An absorbent article as defined in claim 1, wherein the clip device comprises a pair of opposing plates that are configured to engage an edge of the absorbent article when the edge is positioned therebetween.

3. An absorbent article as defined in claim 2, wherein the plates are biased towards each other.

4. An absorbent article as defined in claim 3, wherein the plates are pivotally connected together.

5. An absorbent article as defined in claim 1, wherein each terminal includes a plurality of prongs, the prongs comprising blade members, teeth members, pin members, hook-like members or combinations thereof.

6. An absorbent article as defined in claim 1, wherein the first and second terminals each comprise a single conductive prong, the prong comprising a blade member, a tooth member, or a pin member.

7. An absorbent article as defined in claim 3, wherein the plates are biased towards each other by a spring positioned about a hinge.

8. An absorbent article as defined in claim 2, wherein the plates are integral with each other.

9. An absorbent article as defined in claim 8, wherein the clip device is constructed from a flexible material and the plates are biased toward each other when the clip is placed on the absorbent article.

10. An absorbent article as defined in claim 2, wherein one plate further comprises a backing member capable of receiving the prongs should the prongs extend all the way through the chassis.

11. An absorbent article as defined in claim 2, wherein at least one terminal of the clip member is pivotally connected to the plate about a pivot pin.

12. An absorbent article comprising:
a chassis comprising an outer cover having an interior surface and an exterior surface and an absorbent structure positioned adjacent the interior surface of the outer cover, the chassis including a crotch region positioned in between a front region and a back region, the front region and the back region defining a waist region therebetween;
first and second conductive elements contained in the chassis, the conductive elements extending from the waist region to the crotch region without intersecting, the first and second conductive elements forming part of a circuit that is configured to sense the presence of a substance; and
a first conductive pad member electrically connected to the first conductive element and a second conductive pad member electrically connected to the second conductive element, the conductive pad members being positioned below at least one layer of material of the chassis, the conductive pad members each being configured to electrically connect to a signaling device through the at least one layer of material, and wherein, when a substance is present a signaling device attached to the conductive pad members is activated;
a third conductive element that extends into the back region of the chassis and a fourth conductive element that extends into the front region of the chassis, the third conductive element being electrically connected to a third conductive pad member, while the fourth conductive element being electrically connected to a fourth conductive pad member; and
a signaling device that includes four terminals for attachment to each of the respective pad members, and wherein when the substance is present in the crotch region of the chassis, the first and second conductive elements form a closed circuit, when the substance is present in the back region of the chassis, the first and third conductive elements form a closed circuit, and when the substance is present in the front region, the fourth conductive element forms a closed circuit with the first conductive element, the signaling device being configured to not only indicate when the substance is present in the chassis, but also to indicate which circuits have closed.

13. The absorbent article as defined in claim 12, wherein the signaling device comprises a clip member.

14. The absorbent article as defined in claim 13, wherein the clip member comprises a pair of opposing plates that are configured to engage an edge of the absorbent article when the edge is positioned therebetween.

15. An absorbent article as defined in claim 14, wherein the plates are biased towards each other.

16. An absorbent article as defined in claim 15, wherein the plates are pivotally connected together.

17. An absorbent article as defined in claim 12, wherein each terminal includes a plurality of prongs, the prongs comprising blade members, teeth members, pin members, hook-like members or combinations thereof.

18. An absorbent article as defined in claim 12, wherein the first, second, third, and fourth terminals each comprise a single conductive prong, the prong comprising a blade member, a tooth member, or a pin member.

19. An absorbent article as defined in claim 15, wherein the plates are biased towards each other by a spring positioned about a hinge.

20. An absorbent article as defined in claim 14, wherein the plates are integral with each other.

21. An absorbent article as defined in claim 20, wherein the clip device is constructed from a flexible material and the plates are biased toward each other when the clip is placed on the absorbent article.

22. An absorbent article as defined in claim 17, wherein one plate further comprises a backing member capable of receiving the prongs should the prongs extend all the way through the chassis.

23. An absorbent article as defined in claim 18, wherein one plate further comprises a backing member capable of receiving the prongs should the prongs extend all the way through the chassis.

24. An absorbent article as defined in claim 14, wherein at least one terminal of the clip member is pivotally connected to the plate about a pivot pin.

* * * * *